(12) United States Patent
Li et al.

(10) Patent No.: US 6,995,256 B1
(45) Date of Patent: Feb. 7, 2006

(54) ISOLATION AND CHARACTERIZATION OF A FIBER-SPECIFIC ACTIN PROMOTER FROM COTTON

(75) Inventors: Xuebao Li, Singapore (SG); Lin Cai, Singapore (SG); Ninghui Cheng, Houston, TX (US); Jian-Wei Liu, Singapore (SG)

(73) Assignee: Temasek Life Sciences Laboratory Limited, Singapore (SG)

( * ) Notice: Subject to any disclaimer, the term of this patent is extended or adjusted under 35 U.S.C. 154(b) by 514 days.

(21) Appl. No.: 10/089,557

(22) PCT Filed: Aug. 1, 2000

(86) PCT No.: PCT/SG00/00112

§ 371 (c)(1),
(2), (4) Date: Jul. 18, 2002

(87) PCT Pub. No.: WO02/10413

PCT Pub. Date: Feb. 7, 2002

(51) Int. Cl.
C12N 15/29 (2006.01)

(52) U.S. Cl. .................................... 536/24.1
(58) Field of Classification Search ............... 536/24.1; 800/287
See application file for complete search history.

(56) References Cited

U.S. PATENT DOCUMENTS 5,620,882 A  4/1997  John

OTHER PUBLICATIONS

Miki et al (Oct. 1999, WO 99/53067-A2).*
Kagaya et al (1995, Mol. Gen. Genet. 248 :668-674).*
Benfey et al (1990, Science 250:959-966).*
Benfey et al (1989, EMBO J, 8(8);2195-2202).*
EMBL Accession No. ATU27811, Oct. 3, 1995.
EMBL Accession No. AF059484, Aug. 17, 1998.
EMBL Accession No. AI727771, Jun. 12, 1999.
Shimizu, Y. et al. (1997). "Changes in Levels of mRNAs for Cell Wall-Related Enzymes in Growing Cotton Fiber Cells," *Plant Cell Physiol.* 38(3):375-378.
John, M.E. (1996). "Structural characterization of genes corresponding to cotton fiber nRNA, E6: reduced E6 protein in transgenic plants by antisense gene," *Plant Mol. Biol.* 30:297-306.
Rinehart, J.A. et al. (1996). "Tissue-Specific and Developmental Regulation of Cotton Gene FbL2a," *Plant Physiol.* 112:1331-1341.
Shah, D.M. et al. (1982). Complete nucleotide sequence of a soybean actin gene, *Proc. Natl. Acad. Sci. USA* 79:1022-1026.

* cited by examiner

*Primary Examiner*—David H. Kruse
*Assistant Examiner*—Stuart F. Baum
(74) *Attorney, Agent, or Firm*—Rothwell Figg Ernst & Manbeck

(57) ABSTRACT

The present invention relates to the cotton actin gene CFACT1, and the fiber-specific promoter thereof. These promoters show strong fiber-specific activity.

1 Claim, 4 Drawing Sheets

```
CTGGAGCTCGCGCGCCTGCAGGTCGACACTAGTGGATCCAAAGTAATTCGGCACGAGGGG
TTTCTCACACCGTGCCAATCTATGAAGGATATGCCCTTCCACATGCCATCCTCCGTCTTGA
CCTTGCAGGTCGTGATCTAACCGATGCCTTGATGAAAATTCTTACCGAGAGAGGTTACATG
TTCACCACCACTGCTGAACGGGAAATTGTCCGTGACATGAAGGAGAAGCTTGCTTATGTT
GCCCTGGACTATGAGCAGGAACTGGAGACTGCGAAGAGCAGCTCATCTGTTGAGAAAAAC
TATGAGTTGCCTGACGGACAAGTCATTACTATTGGAGCTGAGAGATTCCGTTGCCCGGAA
GTCCTCTTCCAGCCATCTTTCATCGGGATGGAAGCTGCTGGAATCCATGAAACTACCTACA
ACTCTATCATGAAGTGTGATGTGGATATCAGGAAGGATCTCTACGGTAACATTGTGCTCAG
TGGGGGTTCAACCATGTTCCCTGGTATTGCAGACCGCATGAGCAAGGAGATCACTGCACT
TGCTCCAAGCAGCATGAAGATTAAAGTCGTTGCCCCACCAGAAAAAAAAATACAGTGTCT
GGATTGGAAGGATCTATCTTGGCATCACTCCACACCTTCCAACAAATGTGGATTTCCCAGG
GTGAATTTGATGAATCCGGC
```

```
CTGGAGCTCGCGCGCCTGCAGGTCGACACTAGTGGATCCAAAGTAATTCGGCACGAGGGG
TTTCTCACACCGTGCCAATCTATGAAGGATATGCCCTTCCACATGCCATCCTCCGTCTTGA
CCTTGCAGGTCGTGATCTAACCGATGCCTTGATGAAAATTCTTACCGAGAGAGGTTACATG
TTCACCACCACTGCTGAACGGGAAATTGTCCGTGACATGAAGGAGAAGCTTGCTTATGTT
GCCCTGGACTATGAGCAGGAACTGGAGACTGCGAAGAGCAGCTCATCTGTTGAGAAAAAC
TATGAGTTGCCTGACGGACAAGTCATTACTATTGGAGCTGAGAGATTCCGTTGCCCGGAA
GTCCTCTTCCAGCCATCTTTCATCGGGATGGAAGCTGCTGGAATCCATGAAACTACCTACA
ACTCTATCATGAAGTGTGATGTGGATATCAGGAAGGATCTCTACGGTAACATTGTGCTCAG
TGGGGGTTCAACCATGTTCCCTGGTATTGCAGACCGCATGAGCAAGGAGATCACTGCACT
TGCTCCAAGCAGCATGAAGATTAAAGTCGTTGCCCCACCAGAAAAAAAAATACAGTGTCT
GGATTGGAAGGATCTATCTTGGCATCACTCCACACCTTCCAACAAATGTGGATTTCCCAGG
GTGAATTTGATGAATCCGGC
```

FIG. 1

```
ACTATAGGGCACGCGTGGTCGACGGCCCGGGCTGGTCCTCTAAAGAACAATTGTGTCAAGTCGTTCTTGCCGAGCA
AATCCGAATAGGAGCTTAGAGTAACATCTAACAGACGGACTGCTCCAGCATTAACTGTTTGGTGAAAATGTTAAT
GGTAGTGCTATGTCGAAGTATTTTCATGGAAGGTGTTAAGAATTAATGTTATTGGGATTACTAATTTCTAGTATTAA
TTGTGGTTTGGAAGTTAATATATAATTATTCAATCCTTGTTTTTATTTTTTTTTATAACACAATTACAAATAATTT
ATTTAACTTTGGTTGTTTTCAATTTATGACGGTTAATATTTTAGTTTAATAATTGAGCATTATTATATATTAAATAAA
TAAATCATTGTAATATATGTAAAAATAATTTAAAATATAAATTTATTAATATATATAATAAACTCAATCAAACAAT
AAAAAGATAATAAATTCTTAAATATATAAATTTTTTAAAATAGCTTTTCAGTAAATCTGTCAAACAATAGAAAATA
TTTTTTGCAGGTTCATCCAAACACCAGAAAAGTAAATCATTTTCAGAAAAGTAAATCATTTTTCAGAAATTATTTTT
CGGAAATTATTTTACTGGCAAACAAATGGAGTCTAAGTGTTTCTGTTTTTATTTTTTATTTTTCTATTTAGAGAAACT
AGAAATTGATTTGTCAAATGTCTTTAATCTAGCTTGTTTAGATTAGTTGAAGGGCACAGAACCCGCGTTGTCAAGT
GATTTTGCTGTACTCACTACCTAGATTCTTATTTTCAGTATTGTAAAAGATGGCCGACGGTGAGGCTATTCAACCCC
TCGTCTGTGATAATGGAACTGGAATGGTGAAGGTTAGTTATTTTTTAGACCAAAGCAAACCTGACACCTAGCTTTT
AGACTTGGACAAGGATAAAATCTGTTTAAGTGGGCTTAGCTCAGGCTTCTACATTCAAAGCCTGAATGCAGCTCAG
CTCATTTACATTATATAATTTATAGATATAATAGATACATATATAATACTATAATTTAAACATTAATTTTCTAAATC
AATGGTAAGGCATATTGCACTCAAGAGAGGAGACATAGATTTAGACCTTGGAAACGACATTGTTGGGAAAGGTAT
CTATAATCCATGAACAAGGACCATAAACATGGACATGAAGAATACCCAAAAAAAATATATTTTAAGAAATAGAAA
ATACTATTGGTAGATTTGGGTAAAATATGAGATCATATTATGGACTAAGCCGAGCTTGGGCACATAAGAATTATGA
TGATATCATACACAAACCTGGCCGGTCTATGAACACTTCTAGACCTGAGTCATAATCTCGGTTATTGTTTATTTCTT
TATGAAAAGTAACTTATGGTTAAGCTAATTTTGTCTGTAATGTAGGCCGGTTTTGCTGGTGATGATGCTCCAAGGG
CAGTTTTTCCCAGTATCGTTGGTCGTCCCCGGCACACTGGTGTTATGGTTGGGATGGGTCAGAAGGATGCCTATGT
AGGAGATGAAGCACAATCTAAAGGAGGTATCCTTACTTTGAAATATCCTATTGAGCATGGTATTGTGAGCAATTGG
GATGATATGGAAAAGATCTGGCATCATACATTCTACAACGAACTCCGTGTTGTTCCTGAGGAGCTCCCTGTGCTAC
TCACGGAAGCACCTCTCAACCCCAAGGCCAATAGAGAAAAGAAGACTCAGATCATGTTTGAGACCTTCAATGTAC
CTGCTATGTATGTTGCCATCCAGGCCGTTCTCTCTCTGTATGCCAGTGGTCGTACAACAGGTTTGTTAGACTTGAAA
CTTCTATGAGCTTTTCTCATTTTAATGATATTTTCGAATCATGTTGACACTGGATTATCCCTCTATTGGAACAGGTAT
TGTGCTGGATTCCGGTGATGGTGTTTCTCACATCGTGCCAATCTATGAAGGATATGCCCTTCCACATGCCATCCTCC
GTCTTGACCTTGCAGGTCGTGATCTAACCGATGCCTTGATGAAGATTCTTACCGAGAGAGGTTACATGTTCACCAC
CACTGCTGAACGGGAAATTGTCCGTCACATGAAAGAGAAGCTTGCTTATGTTGCCCTGGACTATGAGCAGGAGCT
GGAGACTGCCAAGAGCAGCTCATCTGTTGAGAAGAACTATGAGTTGCCTGACGGACAAGTTATTACTATTGAAGC
TGAGAGATTCCGTTGCCCGGAAGTCCTCTTCCAGCCATCTTTCATCGGGATGGAAGCTGCTGGAATCCATGAAACT
ACCTACAACTCTATCATGAAGTGTGATGTGGATATCAGGAAGGATCTCTACGGTAACATTGTGCTCAGTGGGGGTT
CAACCATGTTCCCCGGTATTGCAGACCGCATGAGCAAGGAGATCACTGCACTTGCTCCAAGCAGCATGAAGATTA
AGGTCGTTGCGCCACCAGAGAGAAAGTACAGTGTCTGGATTGGAGGATCTATCTTGGCATCACTCAGCACCTTCCA
GCAGGTAAATATATATTTTTATATTTGGCTCTACTTCTTTTGTTTGATGGTTGTCCGACACTGACGTTCTTGCTTTAC
AGATGTGGATTTCCAAGGGTGAGTATGATGAATCCGGTCCATCCATTGTCCACAGGAAGTGCTTCTAAGTTTTGTA
ATTGCTTTTGATGGTGATCTACATTTTGCATTTAGTTGGCTCTTTTTTGGCGTGCCGTGTCAAGTGAACTCAAAAGT
CTGGTTTATGTGCGGGAAGTTAGGGATCATTGTAGGATGGTGTACCTGATATTGACGTATTATTATTTTAGCCTTTC
ACCGTATCACCACCATTAAGCTGATGGGCCCTAAGGAGATGGCGGTGGACGGACAATTGGTGCTTAATTCCTTCCC
TACAATCCATCTTTGAACCATGCTGCTTAAAAGGATGTTTGGAGCGGGAGACTGGATTGTGGTGCTTTTATTTTTTT
ATTTATTTAATATTCAAGGGTTTTGAGAACATTAATGTTAATAGCTATTATTGTACGAGATTT
```

FIG. 2

ISOLATION AND CHARACTERIZATION OF A FIBER-SPECIFIC ACTIN PROMOTER FROM COTTON

TECHNICAL FIELD

The present invention relates to the field of plant molecular biology, in particular to transgenic plants and promoters useful in creating transgenic plants, and more particularly to fiber-specific promoters.

BACKGROUND OF THE INVENTION

Cotton is the most extensively used natural fiber in the textile industry. Annual production of cotton worldwide is over 100 million bales valued at 45 billion U.S. dollars. Although significant improvements have been made in quality and yield of the fibers by means of classical breeding in the past decades, the potential for further improving fiber properties through classical breeding is limited due to requirements for species compatibility and available traits. Genetic engineering provides novel approaches for further improving cotton by introducing genes to create new germplasms with highly desirable characteristics.

Cotton fibers (seed hairs) are single-cell trichomes that undergo rapid and synchronous elongation. Cortical microtubules provide spatial information necessary for the alignment of cellulose microfibrils that confine and regulate cell elongation [Giddings and Staehelin, 1991; Cyr and Palevitz, 1995; Fisher and Cyr, 1995]. Fiber development consists of four overlapping stages (i.e. initiation, primary cell wall formation, secondary cell wall formation and maturation) [Basra and Malik, 1984]. Tubulins and actins may play functionally important roles in developing fiber cells. Mature fiber is a biological composite of cellulose, water, small quantities of proteins, pectins, hemicellulose, mineral substances, wax, small amounts of organic acids, sugars, and pigments that provides excellent wearability and aesthetics [Arthur, 1990; Basra and Malik, 1984; Ryser, 1985]. Many genes are required for the fiber differentiation and development. These genes are differentially expressed during different stages of the fiber development, and so far only a few of the genes involved in the biosynthesis of the large numbers of fiber-specific structural proteins, enzymes, polysaccharides, waxes or lignins have been identified [John and Crow, 1992; John, 1996a; Song and Allen, 1997; Ma et al., 1997; Kawai et al., 1998; Whittaker and Triplett, 1999]. These isolated genes may be considered as having potential application in cotton fiber improvement due to the character of their fiber-specific expression. For example, John has been using fiber-specific gene promoters to produce genetically engineering cotton for altered fibers [John, 1996b, 1997a, 1997b].

A promoter is a DNA fragment that determines temporal and spatial specificity of gene expression during plant and animal development. Many tissue-specific genes and their promoters have been identified and isolated from a wide variety of plants and animals over the past decade, including some cotton tissue-specific genes and promoters (Loguerico et al., 1999; Kawai et al., 1998; Song and Allen, 1997; Ma et al, 1997; John, 1996a; Rinehart et al., 1996; Hasenfratz et al, 1995; John and Peterson, 1994; John and Crow, 1992). A few promoters have been shown to control gene expression in a fiber-specific manner in cotton (Rinehart et al., 1996; John, 1996a; John and Crow, 1992). Some plant tissue-specific promoters can be utilized to express foreign proteins in specific tissues in a developmentally regulated pattern [John, 1996b, 1997a, 1997b].

SUMMARY OF THE INVENTION

A fiber-specific gene (named CFACT1), encoding actin, was isolated from cotton. The isolated complete CFACT1 gene is 3.040 kb long, including a 0.816 kb promoter. The CFACT1 promoter fragment (0.8 kb) was fused with the GUS gene to construct gene expression vectors for analyzing the function of the promoter. Transgenic cotton and tobacco plants with the CFACT1 promoter/GUS fusion gene was identified by Southern blot hybridization. In all the transgenic cotton plants studied, GUS activity was detected only in young fibers, but not in the flower organs such as anthers, petals and sepals, or in leaves and roots. This result, together with Northern blot analysis, indicates that the CFACT1 promoter is fiber-specific in cotton. The promoter controls specific gene expression at the transcriptional level in cotton fibers. The isolated promoter may be used in improving cotton fibers to create new cotton varieties with high fiber quality and yield by gene manipulation.

BRIEF DESCRIPTION OF THE FIGURES

FIG. 1 shows the nucleotide sequence of the cotton CFACT1 gene cDNA (686 bp; SEQ ID NO: 1).

FIG. 2 shows the nucleotide sequence of the cotton CFACT1 gene (3040 bp; SEQ ID NO: 2).

DETAILED DESCRIPTION

Figure 3:
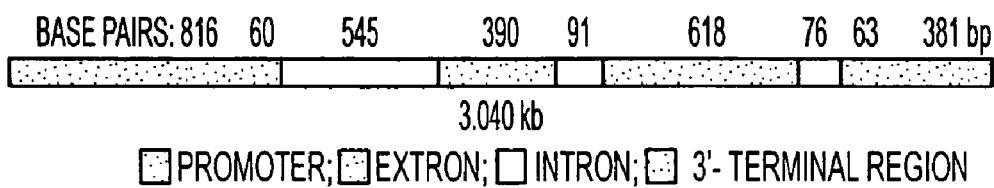
FIG. 3 is a diagram of the structure of the isolated CFACT1 gene.

The CFACT1 promoter is an active fiber-specific promoter in cotton. Results of a Northern blot analysis of cDNAs from a variety of cotton tissues showed that a cDNA clone comprising the CFACT1 gene was strongly expressed in young fibers of 8 and 14 days postanthesis (DPA0, and also expressed in young ovules of 4, 8 and 14 DPA, but less or not at all in other tissues. Sequencing of the cDNA clone revealed that it was 686 bp in length (FIG. 1). The full-length sequence, isolated from a genomic DNA library was found to be 3040 bp in length, including a 0.8 kb promoter fragment, bases 1–816 of which represents the promoter (FIG. 2). A comparison of the nucleotide and predicted polypeptide sequences of the cotton CFACT1 with the data banks revealed that the gene shared high homology at both the amino acid level and the nucleotide level with the known actin genes from some plants such as *Malva pusilla* (AF112538), soybean (U60499), and *Brassica napus* (AF11812), to name a few examples. The CFACT1 gene only shared 71%–93% homology at the amino acid level and 80%–82% identities at the nucleotide level with a known cotton actin gene (AF059484). Moreover, its promoter is different from the promoters of known cotton and non-cotton actin genes, so it is a new actin gene isolated from cotton. Analyzing the CFACT1 gene sequence revealed that it contains four exons and three introns in its open reading frame (FIG. 3). This gene structure is typical of all complete actin genes analyzed so far [Shah et al., 1983; Baird and Meagher, 1987; Nairn et al., 1988; Stranathan et al, 1989; McElroy et al, 1990; Cox et al., 1995; An et al., 1996].

The transcripts of the CFACT1 gene exhibited the highest accumulation (as evidenced by Northern blot analysis) in cotton young fibers of 8 DPA, and then there was a visible decrease in the accumulation of the gene products (mRNA) with further development of the fibers. Comparison of gene expression in different developmental stages of cotton ovules also showed that the gene transcripts accumulated more in 8 DPA ovules than in 4 and 14 DPA, and there was a gradual and visible decrease to an undetectable level in the accumulation of gene products with fiber development from 8 DPA to 28 DPA. This suggests that the gene is specifically expressed with a strict regulation at the transcriptional level during cotton fiber and ovule development, as with other cotton fiber-specific genes [Whittaker and Triplett, 1999; Shin and Brown, 1999; Kawai et al., 1998; John, 1996a; Song and Allen, 1997; Ma et al, 1997; Rinehart et al., 1996; John and Crow, 1992].

The promoter of the CFACT1 gene is 0.8 kb in length, and functions as an active, fiber-specific promoter. A CFACT1 promoter/GUS fusion gene construct was used to transform tobacco and cotton by *Agrobacterium*-mediated gene transfer, using the pBI121 vector containing a CaMV35S promoter/GUS fusion as a positive control. Consistent with the results from Northern blot analysis, the GUS gene driven by the CFACT1 promoter specifically expressed in the young fibers, but not in other tissues, in all the transgenic cotton plants studied, while the GUS activity was detected in all the tissues of positive control cotton plants (35S:GUS). A total of 230 transformed cotton plants were obtained and transplanted in soil to grow to maturation. Similarly, it was found that under the CFACT1 promoter, GUS gene activity was only detected in the seeds and pulps in the more than 20 transgenic tobacco plants studied, suggesting the CFACT1 promoter activity was also tissue-specific in tobacco (the cotton fiber, being an elongated hair of the seed coat, finds histological correspondence in the tobacco seed coat). This result, together with the above Northern blot analysis, indicates that the CFACT1 promoter controls gene specific expression at the transcriptional level in cotton fibers.

Accordingly, one embodiment of the present invention is a promoter that is cotton fiber-specific obtained from the cotton fiber actin gene CFACT1.

Another embodiment of the present invention is a promoter that is cotton fiber-specific comprising the 0.8 kb promoter fragment of the cotton fiber CFACT1 gene, having the sequence of nucleotides 1 through 816 of SEQ ID NO: 2.

Still another embodiment of the present invention is a promoter that is cotton fiber-specific comprising an active fragment of the CFACT1 promoter (nucleic acids 1–816 of SEQ ID NO: 2). An active fragment is a sequence of shorter length than the sequence of nucleic acids 1–816 of SEQ ID NO: 2 which still retains activity as a fiber-specific promoter in cotton. A fragment can comprise excisions, deletions, truncations or substitutions of the sequence of nucleotides 1–816 of SEQ ID NO: 2, or a combination of these.

CFACT1 is strongly expressed in cotton fiber, indicating a direct role in fiber formation and development. Actin is well known in many plants as being involved in cytoskeleton formation and cell expansion. It was based on this idea that genes associated with cytoskeleton formation and cell expansion we sought in the present work. After sequencing, it was decided to follow the CFACT1 as it was an actin gene. Although no any work to demonstrate the function of CFACT1 in transgenic cotton by either over-expression or under-expression has been done, it can be speculated that the CFACT1 is involved in cotton fiber development, as it has a very strong fiber-specific promoter [Delmer, et al., 1995].

The promoters of the present invention are useful in creating transgenic cotton having altered fiber characteristics. The use of the fiber-specific promoters of the present invention permits selective expression of a transgene in the cotton fiber, permitting greater latitude in the types of transgenes employed. Selective expression avoids problems such as the metabolic burden imposed on a transgenic plant by systemic expression of a transgene, or the adverse effects of the expression of a transgene in non-fiber tissues. Examples of expression of desirable genes in cotton fiber, but not in other parts of the cotton plants include: (1) anthocynin genes for colored cotton, (2) silk protein genes from silk worm or spiders for increased strength of cotton fiber, (3) and biosynthesis of polyhydroxybutrate in cotton fiber for improved thermal properties and insulating characteristics [John, et al., 1996]. There are numerous examples in the art of fiber-enhancing genes that could be advantageously linked to the promoters of the present invention, and used to transform cotton using well-known techniques (see, e.g., Umbeck, 1992), to achieve expression of the transgene in transgenic cotton fibers. See e.g., John, 1996b, 1997a, 1997b; John et al., 1996.

EXAMPLE 1

Isolation of Fiber-Specific cDNA Encoding CFACT1 Sequences

Cotton seeds were surface-sterilized with 70% ethanol for 30–60 seconds and 10% $H_2O_2$ for 30–60 minutes, followed by washing with sterile water. The seeds germinated on ½ MS medium on light at 28° C. in a culture room, and cotyledons and hypocotyls cut from sterile seedlings were used as transformation explant materials. Cotton plants were grown in pots for DNA and RNA extraction.

Total RNA was extracted from young fibers, ovaries, anthers, petals, sepals, leaves and roots of cotton by using the guanidinium thiocyanate method or SV Total RNA Isolation System (Promega). Poly(A)+ RNA was purified by using oligo(dT)-cellulose spin columns from an mRNA purification kit (Pharmacia Biotech). Cotton cDNA was synthesized by using a cDNA synthesis kit (Pharmacia Biotech). Cotton cDNA libraries were constructed by inserting the cDNA fragments into the ZAP express vector (Stratagene).

Poly(A)+ RNAs from cotton young fibers of about 8 and 14 days postanthesis (DPA), respectively, were converted to cDNAs which were used to construct cotton cDNA libraries. From the fiber cDNA libraries, about 200 cDNA clones were randomly picked out and subsequently sequenced. Some clones with potential involvement in cell expansion were selected according to the sequence data.

To find cDNA clones whose transcripts are specifically expressed in cotton fibers, the expression pattern of the selected cDNA clones was analyzed by Northern blot hybridization with total RNAs isolated from cotton fibers, ovules, anthers, petals, sepals, squares, leaves and roots, using probes from the clones. RNA samples from the different cotton tissues were separated on agarose-formaldehyde gels, and transferred onto Hybond-N nylon membranes by capillary blotting. RNA Northern blots were hybridized in ExpressHyb solution (Clontech) at 68° C. with $^{32}P$ cDNA probes prepared by random labeling (Promega Prime-a-Gene Labeling System). After hybridization, the blots were washed at 68° C. in 0.1×SSC, 0.5% SDS for 30–60 minutes. The experimental results showed that one cDNA clone strongly expressed in young fibers of 8 and 14

DPA, and also expressed in young ovules of 4, 8 and 14 DPA, but less or not at all in other tissues.

Figure 4:
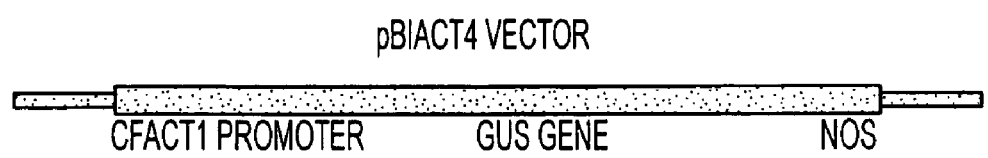
FIG. 4 shows the construct of the CFACT1 promoter fused with the GUS gene in an expression vector.

PCR fragments and cDNA fragments were subcloned into vectors, and plasmid DNA prepared with a Qiagen plasmid kit was used as templates in PCR reactions. The PCR products were sequenced by autosequencer. One clone was found to be a 686 bp CFACT1 cDNA fragment (FIG. 1) encoding a part of the actin polypeptide. Northern blot hybridization revealed the CFACT1 cDNA transcripts accumulated largely in young fibers of 8 and 14 DPA, and also accumulated more or less in young ovules of 4, 8, 14 and 21 DPA. But, these transcripts were neither detected in RNA from ovules of 28 DPA, nor in those from anthers, petals, sepals, leaves and roots (FIG. 4). This result suggests the CFACT1 cDNA expression is fiber-specific in cotton. Comparison of the CFACT1 cDNA sequence with that of a known cotton actin cDNA from the data banks (D88414), which is only 1.079 kb in length and not a complete actin cDNA, showed that both cDNAs share a high level of homology (97% identities in amino acid level and 96% identities in nucleic acid level).

Total RNAs from different tissues of cotton were used to reverse-transcribe first-strand cDNAs which were used as templates in differential display PCR reactions. Differential display analysis was carried out by using a differential display kit (Clontech). First-strand cDNA was synthesized with 2 pg total RNA as starting materials of reverse transcription and oligo(dT) as primers at 42° C. for 1 hour. Differential display PCR reactions were carried out with a initial cycle consisting of 94° C. for 5 minutes, 40° C. for 5 minutes and 68° C. for 5 minutes, followed by two cycles consisting of 94° C. for 2 minutes and 40° C. for 5 minutes and 68° C. for 5 minutes, and then 25 cycles consisting of 94° C. for 1 minute and 60° C. for 1 minute and 68° C. for 2 minutes, and a final extension at 68° C. for 7 minutes. Target differential display bands were excised and reamplified for further analysis. Reproducible fiber-specific differential display products were targeted for further analysis. The cDNA in each target band was harvested and regenerated by PCR amplification. The isolated cDNA was subsequently subcloned into vectors and sequenced.

The Northern blot analysis showed that the transcripts of the CFACT1 gene exhibited their highest accumulation in cotton young fibers of 8 DPA, and then there was a visible decrease in the accumulation of the gene products (mRNA) with further development of the fibers. Comparison of gene expression in different developmental stages of cotton ovules also showed that the gene transcripts accumulated more in 8 DPA ovules than in 4 and 14 DPA, and there was a gradual and visible decrease to an undetectable level in the accumulation of gene products with fiber development from 8 DPA to 28 DPA. This suggests that the gene is specifically expressed with a strict regulation at the transcriptional level during cotton fiber and ovule development, as is seen with other cotton fiber-specific genes [Whittaker and Triplett, 1999; Shin and Brown, 1999; Kawai et al., 1998; John, 1996a; Song and Allen, 1997; Ma et al, 1997; Rinehart et al., 1996; John and Crow, 1992].

EXAMPLE 2

Isolation and Structural Analysis of the CFACT1 Gene

Total DNA was extracted and purified from leaves of cotton plants by using the following method. Liquid $N_2$ was added to 4 g of leaf tissues, and the leaves were homogenized thoroughly. 20 ml ice-cold extraction buffer (63 g/L glucose, 0.1 M Tris.HCl (pH 8.0), 5 mM EDTA, 20 g/L PVP-40, 1 g/L DIECA, 1 g/L ascorbic acid, 2 ml/L beta-mercaptoethanol) was added to the homogenized tissues in a 50 ml tube and centrifuged at 2500 rpm for 15 minutes. After removing the supernatant, 10 ml lysis buffer was added to each tube. The resuspended pellets were incubated at 65° C. for 30 minutes. 10 ml chloroform was added to each tube, mixed with the samples and centrifuged at 3500 rpm for 10 minutes. The supernatant was transferred to a clean tube, and chloroform extraction was repeated one more time. The supernatant was transferred to a clean tube, and 0.6 volume isopropanol was added to each tube for DNA precipitation. After centrifuging at 3500 rpm for 30 minutes, the DNA was washed with 70% ethanol. The isolated genomic DNA was then dissolved in sterile water or TE (10 mM Tris.HCl, 1 mM EDTA) for use.

Cotton genomic DNA libraries were constructed from leaves of cotton plants. DNA was partially digested with BamH I, and the DNA fragments were cloned in the BamH I site of the ZAP expression vector (Stratagene).

Genome Walker libraries were constructed by using Universal Genome Walker kit (Clontech). Genomic DNA from leaves of cotton plants was digested with five restriction enzymes respectively, and then purified by phenol/chloroform and precipitated by ethanol. Digested DNA was ligated to Genome Walker adaptors. Two rounds of Genome Walker PCR reactions were carried out successively. 1 µl of each Genome Walker DNA library was used as templates in the primary PCR, and the primary PCR products were used as templates in secondary PCR. The PCR was started at 95° C. for 1 minute, followed by 35 cycles consisting of 95° C. for 15 seconds and 68° C. for 4 minutes, and a final extension at 68° C. for 6 minutes. Target PCR bands were cut out and purified by Geneclean kit (Bio 101).

Two overlapping fragments, which covered the full length of the CFACT1 gene, were isolated by the Genome Walker approach and completely sequenced. The complete CFACT1 gene was 3040 bp in length, including a 0.8 kb promoter (FIG. 2). Comparing the nucleotide and predicted polypeptide sequences of the cotton CFACT1 gene with the data banks, it was found that the gene shared high homology at both the amino acid level and the nucleotide level with the known actin genes from plants such as *Malva pusilla* (AF112538), soybean (U60499), *Brassica napus* (AF11812), to name a few examples. The CFACT1 gene only shared 71%–93% homology at the amino acid level and 80%–82% identities at the nucleotide level with a known cotton actin gene (AF059484). Moreover, its promoter is different from the promoters of known cotton and non-cotton actin genes, so it is a new actin gene isolated from cotton. Analyzing the CFACT1 gene sequence revealed that it contains four exons and three introns in its open reading frame (FIG. 3). This gene structure is typical of all complete actin genes analyzed so far [Shah et al., 1983; Baird and Meagher, 1987; Nairn et al., 1988; Stranathan et al, 1989; McElroy et al, 1990; Cox et al., 1995; An et al., 1996].

EXAMPLE 3

Functional Analysis of the CFACT1 Promoter

To characterize the function of CFACT1 promoter, the 0.8 kb CFACT1 promoter was linked to the GUS gene in pBI101, to construct gene expression vector (FIG. 4). Cotton and tobacco were transformed by *Agrobacterium tumefaciens* containing the CFACT1 promoter/GUS fusion gene, using the pBI121 vector containing a CaMV35S promoter/ GUS fusion as a positive control. The CaMV35S promoter is active in all the tissues of cotton and other plants and is a constitutive promoter [Odell et al., 1985; Ow et al., 1987; McCabe and Martinell, 1993]. A binary vector containing either the CFACT1 promoter/GUS fusion gene or the CaMV35S promoter/GUS fusion control was transferred into *Agrobacterium tumefaciens* strain LBA 4404. Cotton explants for transformation were obtained from cotton seedlings grown as in Example 1. Tobacco explant material was obtained from tobacco seedlings. Tobacco seeds were surface-sterilized with 70% ethanol for 30–60 seconds and 0.1% $HgCl_2$ for 15 minutes, followed by washing with sterile water. The seeds were germinated on ½ MS medium on light at 28° C. in culture room, and leaves cut from sterile seedlings for use as explants for transformation. Cotton cotyledon and hypocotyl explants and tobacco leaf explants were transformed by the *Agrobacterium* with the vectors and transformed plants were transplanted to soil in greenhouse for growing to maturity.

Tobacco leaves were cut into about 2×2 cm pieces, and immersed in *Agrobacterium* suspension for 5 minutes. The infected tobacco explants were cultivated on MS medium with 1 mg/L 6-BA for 48 hours at 28° C., and then transferred onto selection MS medium containing 100 mg/L kanaymcin and 1 mg/L 6-BA for 20–30 days for selecting transformed shoots (kanamycin-resistant shoots). The transformed shoots were cut from the calli and rooted on MS medium with 50–100 mg/L kanamycin. The transformed tobacco plants were transplanted to soil in greenhouse for growing to maturity.

The cotyledon and hypocotyl were used as explants for cotton transformation. Cotton seeds were surface-sterilized with 70% ethanol for 30 seconds and 10% $H_2O$ for 60 minutes, followed by washing with sterile water. These seeds were incubated in the sterile water at 28° C. The seeds sprouted overnight. The embryos were taken out and put on the IM medium (½(MS (macronutrients, micronutrients, EDTA-Fe)+VB1 10 mg/L+VB6 1 mg/L+VPP 1 mg/L+Myo-Insitol 100 mg/L)+phytogel 2 g/L pH=6.4) at 28° C. for 7 days. The cotyledon and hypocotyl of cotton were used as explants for transformation. After cutting into 5 mm² (mm) piece, the explants were soaked in the *Agrobacterium tumefaciens* strain LBA 4404 suspension ($OD_{600}$=0.2–0.4) for 15 minutes. Then the explants were put on CM medium (MS macronutrients, micronutrients, EDTA-Fe)+VB1 10 mg/L+VB6 1 mg/L+VPP 1 mg/L+Myo-Insitol 100 mg/L+2.4-D 0.1 mg/L+KT 0.1 mg/L+Glucose 30 g/L+$MgCl_2$ 0.7 mg/L+phytogel 2 g/L pH=6.4) at 24° C. for 2 days. After washing with liquid MS medium, the explants were put on the SM medium (MS (macronutrients, micronutrients, EDTA-Fe)+VB1 10 mg/L+VB6 1 mg/L+VPP 1 mg/L+Myo-Insitol 100 mg/L+2.4-D 0.1 mg/L+KT 0.1 mg/L+Glucose 30 g/L+$MgCl_2$ 0.7 mg/L+phytogen 2 g/L+Kanamycin 50 mg/L+Cefutoxime 200 mg/L pH=6.4) on light at 28° C. in culture room for selecting and the subculture was per month. After 2–3 months subculturing on SM, the calli were induced from explants. The calli were transferred on DM medium (MS (macronutrients, micronutrients, EDTA-Fe)+VB1 10 mg/L+VB6 1 mg/L+VPP 1 mg/L+Myo-Insitol 100 mg/L+$KNO_3$ 19 g/L+$MgCL_2$ 0.7 mg/L Glucose 30 g/L phytogel 3 g/L pH 6.4) and subcultured per month. After about 5 months, the somatic embryos began to form. Continuing to culture the young embryos on DM medium until they develop into maturity. The mature embryos were transferred on GM medium (½(MS (macronutrients, micronutrients, EDTA-Fe)+VB1 10 mg/L+VB6 1 mg/L+VPP 1 mg/L+Myo-Insitol 100 mg/L)+NAA 0.01 mg/L+Glucose 30 g/L+phytogel 3.5 g/L pH=6.4) in the box for developing into plantlets. And then the plantlets were transplanted in the soil for the plant growing and collecting the transgenic seeds.

Transgenic tobacco and cotton plants possessing the chimeric CFACT1 promoter/GUS gene (or 35S:GUS gene), and non-transformed plants as negative controls, were analyzed by DNA Southern blot hybridization and by GUS histochemical assay. Total genomic DNA from cotton and tobacco leaves were digested with restriction enzymes, separated on agarose gels, and transferred onto Hybond-N nylon membranes by capillary blotting. DNA Southern blots were hybridized in ExpressHyb solution (Clontech) at 68° C. with $^{32}$P-DNA probes prepared by random labeling (Promega Prime-a-Gene Labeling System). After hybridization, the blots were washed at 68° C. in 0.1×SSC, 0.5% SDS for 30–60 minutes. The $^{32}$P-labeled nylon membranes were exposed to X-ray film at −70° C. for autoradiography. Southern blot analysis demonstrated that the CFACT1 promoter/GUS fusion gene was integrated into cotton and tobacco genomes.

Histochemical assays for GUS activity in transgenic tobacco and cotton plants were conducted according to the protocol described previously by Jefferson et al. (1987) with some modifications. Fresh tissues from the plants were incubated in X-gluc (5-bromo-4-chloro-3-indolylglucuronide) solution consisting of 0.1 M sodium phosphate (pH 7.0), 10 mM ethylene diaminetetraacetic acid (EDTA), 0.5 mM potassium ferrocyanide and 0.5 mM potassium ferricyanide, and 0.1% X-gluc (Clontech Chemical) overnight. The stained plant materials were then cleared and fixed by rinsing with 100% and 70% ethanol successively, and the samples were examined and photographed directly or under a microscope. A total of 230 transformed cotton plants, which belong to 21 transformed lines, were obtained and transplanted in soil to grow to maturity. In all the transgenic cotton plants studied, GUS activity was detected only in young fibers, but not in the flower organs such as anthers, petals and sepals, or in leaves and roots. In comparison, plants transformed with the positive control pBI121 (35S: GUS) exhibited strong GUS activity in all the tissues, and the non-transformed plants showed no GUS activity in fibers as well as other tissues when stained in X-gluc solution under the same condition as transgenic plant tissues. In more than 20 transgenic tobacco plants studied, the GUS gene driven by CFACT1 promoter expressed only in seeds and pulps, suggesting that the CFACT1 promoter is also tissue-specific in tobacco. These results indicate that the CFACT1 promoter directs gene specific expression at the transcriptional level in cotton fibers.

REFERENCES

An Y Q, Huang S, McDowell J M, 1996. Conserved expression of the *Arabidopsis* ACT1 and ACT3 actin subclass in organ primordia and mature pollen. Plant Cell, 8(1):15–30.

Arthur J C, 1990. In Polymers: Fibers and Textile, A Compendium, ed. Kroschwitz, J I. (Wiley, N.Y.), pp. 118–141.

Baird W V and Meagher R B, 1987. A complex gene superfamily encodes actin in petunia. EMBO J., 6(11): 3223–31.

Basra A S and Malik C P, 1984. Development of the cotton fiber. Int. Rev. Cytol. 89:65–113.

Chu B, Wilson T J, McCune-Zierath C, Snustad D P, Carter J V., 1998. Two beta-tubulin genes, TUB1 and TUB8, of *Arabidopsis* exhibit largely nonoverlapping patterns of expression. Plant Mol. Biol., 37(5):785–90.

Cox G M, Rude T H, Dykstra C C, 1995. The actin gene from *Cryptococcus neoformans*: structure and phylogenetic analysis. J. Med. Vet. Mycol., 33(4):261–6.

Cyr R J and Palevitz B A, 1995. Organization of cortical microtubules in plant cells. Curr. Opin. Cell Biol., 7:65–71.

Delmer D P, Pear J R, Andrawis A., Stalker D M, 1995. Genes encoding small GTP-binding proteins analogous to mammalian rac are preferentially expressed in developing cotton fibers. Mol. Gen Genet 248(1):43–51.

Fisher D D and Cyr R J, 1998. Extending the microtubule/microfibril paradigm. Plant Physiol., 116:1043–51.

Giddings T H and Staehelin L A, 1991. Microtubule-mediated control of microfibril deposition: a re-examination of the hypothesis. In C W Lloyd, ed., The Cytoskeletal Basis of Plant Growth and Form. Academic Press, London, pp. 85–99.

Hasenfratz M P, Tsou C L, Wilkins T A, 1995. Expression of two related vacuolar H(+)-ATPase 16-kilodalton proteolipid genes is differentially regulated in a tissue-specific manner. Plant Physiol., 108(4): 1395–404.

Jefferson R A, 1987. Assaying chimeric genes in plants: the GUS gene fusion system. Plant Mol. Biol. Rep., 5:387–405.

Jefferson R A, Kavanagh T A, Bevan M W, 1987. GUS fusion: p-glucuronidase as a sensitive and versatile gene fusion marker in higher plants. EMBO J., 6:3901

John M E and Crow L J, 1992. Gene expression in cotton fiber: cloning of the mRNAs. Proc. Natl. Acad. Sci. USA, 89(13):5769–73.

John M E and Peterson M W, 1994. Cotton pollen-specific polygalacturonase mRNA: tissue and temporal specificity of its promoter in transgenic tobacco. Plant Mol. Biol., 26(6):1989–93.

John M E, 1996a. Structural characterization of genes corresponding to cotton fiber mRNA, E6: reduced E6 protein in transgenic plants by antisense gene. Plant Mol. Biol., 30(2):297–306.

John, M E, 1996b. Genetically engineering cotton plants for altered fiber, U.S. Pat. No. 5,495,070.

John, M E and Keller, G, 1996. Metabolic pathway engineering in cotton: Biosynthesis of polyhydroxybutrate in fiber cells. Proc. Natl. Acad. Sci. USA 93, 12768–12773).

John, M E, 1997a. Transgenic cotton plants producing heterologous polyhydroxy(e) butyrate bioplastic, U.S. Pat. No. 5,602,321.

John, M E, 1997b. Genetically engineering cotton plants for altered fiber, U.S. Pat. No. 5,620,882 (1997).

Kang M S, Choi Y J, Kim M C, Lim C O, Hwang I, Cho M J., 1994. Isolation and characterization of two beta-tubulin cDNA clones from rice. Plant Mol. Biol., 26(6): 1975–9.

Kawai M, Aotsuka S, Uchimiya H, 1998. Isolation of a cotton CAP gene: a homologue of adenylyl cyclase-associated protein highly expressed during fiber elongation. Plant Cell Physiol., 39(12):1380–3.

Liaud M F, Brinkmann H, Cerff R., 1992. The beta-tubulin gene family of pea: primary structures, genomic organization and intron-dependent evolution of genes. Plant Mol. Biol., 18(4):639–51.

Loguerico L L, Zhang J Q, Wilkins T A, 1999. Differential regulation of six novel MYB-domain genes def two distinct expression patterns in allotetraploid cotton. Mol. Gen. Genet., 261(4/5):660–71.

Ma D P, Liu H C, Tan H, Creech R G, Jenkins J N, Chang Y F, 1997. Cloning and characterization of a cotton lipid transfer protein gene specifically expressed in fiber cells. Biochim. Biophys. Acta, 1344(2): 111–4.

McCabe D E and Martinell B J, 1993. Transformation of elite cotton cultivars via particle bombardment of meristems. Biotechnology, 11:596–8.

McElroy D, Rothenberg M, Reece K S, Wu R, 1990. Characterization of the rice actin gene family. Plant Mol. Biol., 15(2):257–68.

Nairn C J, Winesett L, Ferl R J, 1988. Nucleotide sequence of an actin gene from *Arabidopsis thaliana*. Gene, 65(2): 247–57.

Odell J T, Nagy F, Chua N-H, 1985. Identification of DNA sequences required for activity of the cauliflower mosaic virus 35S promoter. Nature, 313:810–2.

Okamura S, Naito K, Sonehara S, Ohkawa H, Kuramori S, Tatsuta M, Minamizono M, Kataoka T., 1997. Characterization of the carrot beta-tubulin gene coding a divergent isotype, beta-2. Cell Struct. Funct., 22 (2):291–8.

Okamura S, Okahara K, Iida T, Ozaki M, Asano S, Morita M, Imanaka T, 1999. Isotype-specific changes in the amount of beta-tubulin RNA in synchronized tobacco BY2 cells. Cell Struct. Funct., 24 (3): 117–22.

Ow D W, Jacobs J D, Howell S H, 1987. Functional regions of the cauliflower mosaic virus 35S RNA promoter determined by use of the firefly luciferase gene as a reporter of promoter activity. Proc. Natl. Acad. Sci. USA, 84:4870–4.

Rinehart J A, Peterson M W, John M E, 1996. Tissue-specific and developmental regulation of cotton gene FbL2A. Demonstration of promoter activity in transgenic plants. Plant Physiol., 112(3):1331–41.

Ryser U, 1985. Cell wall biosynthesis in differentiating cotton fibers. Eur. J. Cell Biol., 39:236–56.

Shah D M, Highrower R C, Meagher R B, 1983. Genes encoding actin in higher plants: intron positions are highly conserved but the coding sequences are not. J. Mol. Appl. Genet., 2(1): 111–26.

Shin H and Brown R M jr, 1999. GTPase activity and biochemical characterization of a recombinant cotton fiber annexin. Plant Physiol., 119(3):925–34.

Song P and Allen R D, 1997. Identification of a cotton fiber-specific acyl carrier protein cDNA by differential display. Biochim. Biophys. Acta, 135I(1):305–12.

Snustad D P, Haas N A, Kopczak S D, Silflow C D., 1992. The small genome of *Arabidopsis* contains at least nine expressed beta-tubulin genes. Plant Cell, 4(5):549–56.

Stranathan M, Hastings C, Trinh H, 1989. Molecular evolution of two actin genes from carrot. Plant Mol. Biol., 13(4):375–83.

Taylor M A, Wright F, Davies H V., 1994. Characterization of the cDNA clones of two beta-tubulin genes and their expression in the potato plant (*Solanum tuberosum* L.). Plant Mol. Biol., 26(3):1013–18.

Tonoike H, Han I S, Jongewaard I, Doyle M, Guiltinan M, Fosket D E, 1994. Hypocotyl expression and light down-regulation of the soybean tubulin gene, tubB1. Plant J., 5(3):343–51.

Umbeck, Paul, 1992. Genetic engineering of cotton plants and lines, U.S. Pat. No. 5,159,135.

Villemur R, Haas N A, Joyce C M, Snustad D P, Silflow C D, 1994. Characterization of four new beta-tubulin genes and their expression during male flower development in maize (*Zea mays* L.). Plant Mol. Biol., 24(2):295–315.

Whittaker D J and Triplett B A, 1999. Gene-specific changes in alpha-tubulin transcript accumulation in developing cotton fibers. Plant Physiol., 121(1):181–8.

We claim:

1. An isolated cotton fiber-specific promoter comprising a 0.8 kb fragment of the promoter of the cotton actin gene CFACT1 having the nucleotide sequence of 1 through 816 of SEQ ID NO:2.

* * * * *

SEQUENCE LISTING

<160> NUMBER OF SEQ ID NOS: 2

<210> SEQ ID NO 1
<211> LENGTH: 685
<212> TYPE: DNA
<213> ORGANISM: Gossypium sp.

<400> SEQUENCE: 1

```
ctggagctcg cgcgcctgca ggtcgacact agtggatcca aagtaattcg gcacgagggg      60
tttctcacac cgtgccaatc tatgaaggat atgcccttcc acatgccatc ctccgtcttg     120
accttgcagg tcgtgatcta accgatgcct tgatgaaaat tcttaccgag agaggttaca     180
tgttcaccac cactgctgaa cgggaaattg tccgtgacat gaaggagaag cttgcttatg     240
ttgccctgga ctatgagcag gaactggaga ctgcgaagag cagctcatct gttgagaaaa     300
actatgagtt gcctgacgga caagtcatta ctattggagc tgagagattc cgttgcccgg     360
aagtcctctt ccagccatct ttcatcggga tggaagctgc tggaatccat gaaactacct     420
acaactctat catgaagtgt gatgtggata tcaggaagga tctctacggt aacattgtgc     480
tcagtggggg ttcaaccatg ttccctggta ttgcagaccg catgagcaag gagatcactg     540
cacttgctcc aagcagcatg aagattaaag tcgttgcccc accagaaaaa aaatacagt      600
gtctggattg gaaggatcta tcttggcatc actccacacc ttccaacaaa tgtggatttc     660
ccagggtgaa tttgatgaat ccggc                                           685
```

<210> SEQ ID NO 2
<211> LENGTH: 3041
<212> TYPE: DNA
<213> ORGANISM: Gossypium sp.

<400> SEQUENCE: 2

```
actatagggc acgcgtggtc gacggcccgg gctggtcctc taaagaacaa ttgtgtcaag      60
tcgttcttgc cgagcaaatc cgaataggag cttagagtaa catctaacag acggactgct     120
ccagcattaa ctgtttggtg aaaatgttaa tggtagtgct atgtcgaagt attttcatgg     180
aaggtgttaa gaattaatgt tattgggatt actaatttct agtattaatt gtggtttgga     240
agttaatata taattattca atccttgttt tttatttttt tttataaca caattacaaa      300
taatttattt aactttggtt gttttcaatt tatgacggtt aatatttag tttaataatt      360
gagcattatt atatattaaa taaataaatc attgtaatat atgtaaaaat aatttaaaat     420
ataaatttat taatatatat aataaactca atcaaacaat aaaaagataa taaattctta     480
aatatataaa tttttttaaaa tagcttttca gtaaatctgt caaacaatag aaaatatttt     540
ttgcaggttc atccaaacac cagaaaagta aatcattttc agaaaagtaa atcatttttc     600
agaaattatt tttcggaaat tatttttactg gcaaacaaat ggagtctaag tgtttctgtt     660
tttattttt attttctat ttagagaaac tagaaattga tttgtcaaat gtctttaatc      720
tagcttgttt agattagttg aagggcacag aacccgcgtt gtcaagtgat tttgctgtac     780
tcactaccta gattcttatt ttcagtattg taaaagatgg ccgacggtga ggctattcaa     840
cccctcgtct gtgataatgg aactggaatg gtgaaggtta gttattttttt agaccaaagc    900
aaacctgaca cctagctttt agacttggac aaggataaaa tctgtttaag tgggcttagc     960
tcaggcttct acattcaaag cctgaatgca gctcagctca tttacattat ataatttata    1020
gatataatag atacatatat aatactataa tttaaacatt aattttctaa atcaatggta    1080
```

-continued

```
aggcatattg cactcaagag aggagacata gatttagacc ttggaaacga cattgttggg    1140
aaaggtatct ataatccatg aacaaggacc ataaacatgg acatgaagaa tacccaaaaa    1200
aaatatattt taagaaatag aaaatactat tggtagattt gggtaaaata tgagatcata    1260
ttatggacta agccgagctt gggcacataa gaattatgat gatatcatac acaaacctgg    1320
ccggtctatg aacacttcta gacctgagtc ataatctcgg ttattgttta tttcttatg    1380 aaaagtaact tatggttaag ctaattttgt ctgtaatgta ggccggtttt gctggtgatg    1440
atgctccaag ggcagttttt cccagtatcg ttggtcgtcc ccggcacact ggtgttatgg    1500
ttgggatggg tcagaaggat gcctatgtag gagatgaagc acaatctaaa ggaggtatcc    1560
ttactttgaa atatcctatt gagcatggta ttgtgagcaa ttgggatgat atggaaaaga    1620
tctggcatca tacattctac aacgaactcc gtgttgttcc tgaggagctc cctgtgctac    1680
tcacggaagc acctctcaac cccaaggcca atagagaaaa gaagactcag atcatgtttg    1740
agaccttcaa tgtacctgct atgtatgttg ccatccaggc cgttctctct ctgtatgcca    1800
gtggtcgtac aacaggtttg ttagacttga aacttctatg agcttttctc attttaatga    1860
tattttcgaa tcatgttgac actggattat ccctctattg gaacaggtat tgtgctggat    1920
tccggtgatg gtgtttctca catcgtgcca atctatgaag gatatgccct tccacatgcc    1980
atcctccgtc ttgaccttgc aggtcgtgat ctaaccgatg ccttgatgaa gattcttacc    2040
gagagaggtt acatgttcac caccactgct gaacgggaaa ttgtccgtca catgaaagag    2100
aagcttgctt atgttgccct ggactatgag caggagctgg agactgccaa gagcagctca    2160
tctgttgaga agaactatga gttgcctgac ggacaagtta ttactattga agctgagaga    2220
ttccgttgcc cggaagtcct cttccagcca tctttcatcg ggatggaagc tgctggaatc    2280
catgaaacta cctacaactc tatcatgaag tgtgatgtgg atatcaggaa ggatctctac    2340
ggtaacattg tgctcagtgg gggttcaacc catgttcccc ggtattgcag accgcatgag    2400
caaggagatc actgcacttg ctccaagcag catgaagatt aaggtcgttg cgccaccaga    2460
gagaaagtac agtgtctgga ttggaggatc tatcttggca tcactcagca ccttccagca    2520
ggtaaatata tattttata tttggctcta cttctttgt ttgatggttg tccgacactg    2580
acgttcttgc tttacagatg tggatttcca agggtgagta tgatgaatcc ggtccatcca    2640
ttgtccacag gaagtgcttc taagttttgt aattgctttt gatggtgatc tacattttgc    2700
atttagttgg ctcttttttg gcgtgccgtg tcaagtgaac tcaaaagtct ggtttatgtg    2760
cgggaagtta gggatcattg taggatggtg tacctgatat tgacgtatta ttattttagc    2820
ctttcaccgt atcaccacca ttaagctgat gggccctaag gagatggcgg tggacggaca    2880
attggtgctt aattccttcc ctacaatcca tctttgaacc atgctgctta aaaggatgtt    2940
tggagcggga gactggattg tggtgctttt attttttttat ttatttaata ttcaagggtt    3000
ttgagaacat taatgttaat agctattatt gtacgagatt t                        3041
```